United States Patent [19]

Stone

[11] Patent Number: 5,445,965
[45] Date of Patent: Aug. 29, 1995

[54] PROCESS AND APPARATUS FOR TESTING FOR SUBSTANCES IN LIQUIDS

[75] Inventor: Marcia J. Stone, Wellesley, Mass.

[73] Assignee: Hybrivet Systems, Inc., Natick, Mass.

[21] Appl. No.: 257,430

[22] Filed: Jun. 8, 1994

Related U.S. Application Data

[63] Continuation of Ser. No. 2,834, Jan. 15, 1993, abandoned.

[51] Int. Cl.6 .......................................... G01N 33/20
[52] U.S. Cl. ........................................ 436/81; 436/77; 436/169; 422/61
[58] Field of Search ............... 422/58, 61; 436/77, 436/81, 169

[56] References Cited

U.S. PATENT DOCUMENTS

| | | | |
|---|---|---|---|
| 3,477,822 | 11/1969 | Hamilton | 422/61 |
| 3,480,398 | 11/1969 | Hamilton | 422/61 |
| 3,582,283 | 3/1970 | Mirasol | 422/61 |
| 3,713,779 | 1/1973 | Sirago et al. | 422/61 |
| 3,715,189 | 2/1973 | Nighohossian et al. | 422/61 |
| 3,940,448 | 6/1960 | Furlong | 422/61 |

OTHER PUBLICATIONS

A.O.A.C. Official Methods of Analysis Book, pp. 460–468 (1984).

*Primary Examiner*—Lyle A. Alexander
*Attorney, Agent, or Firm*—Burns, Doane, Swecker & Mathis

[57] ABSTRACT

A method and apparatus for the detection of nutrients and contaminants in a liquid sample. The sample is added to a container which is then capped with a cap assembly which contains crushable reagent containers. As the cap is tightened, the crushable capsules release reagent which reacts with the substance to be detected, causing a detectable color change. The level of the substance in the sample correlates with the color change which can be quantitated by reading the reaction product in a spectrophotometer, or by comparing to known standards. The method is especially suitable for the detection of heavy metal contaminants such as lead, in drinking water.

26 Claims, 3 Drawing Sheets

PROCESS AND APPARATUS FOR TESTING FOR SUBSTANCES IN LIQUIDS

This application is a continuation of application Ser. No. 08/002,834, filed Jan. 15, 1993, now abandoned.

BACKGROUND OF THE INVENTION

1. Field of the Invention

This invention relates to a method and apparatus for detecting contaminants, and in particular, heavy metal contaminants. More specifically, the present invention relates to a test system wherein a sample is placed in a bottle, the bottle is capped, and crushable reagent capsules are broken, releasing compounds which react with the contaminant and produce a detectable color change specific for the contaminant. The present invention is especially well suited for testing water for the presence of nutrients or contaminants such as lead.

2. Background of the Invention

Contamination of the environment has been increasing steadily for years as the use of metals, chemicals, pesticides, and bacterial organisms has increased. Even though the toxicity of various metals has been known for centuries, it is only recently that there has been a serious increase in interest in minimizing human exposure to such metals. Current public awareness of such pollutants and their associated hazards has created a consumer demand for products that are capable of determining the presence of unwanted and potentially dangerous materials.

Some of the more toxic metals include lead, cadmium, mercury, barium, chromium and beryllium. Lead, in particular, has been subject to much attention due to its presence in articles or paints commonly found in the home. See, for example, "A Simple Direct Estimation of Ultramicroquantities of Lead in Drinking Water Using Sodium Rhodizonate" by E. Jungreis and M. Nechama, *Microchemical Journal*, vol. 34, pp. 219–221 (1986); U.K. Patent Application No. 2 025 047 A; "A Simplified Method for Detection of Lead Contamination of Soil" by J. Preer and G. Murchison, Jr., *Environmental Pollution* (Series B), vol. 12, pp. 1–13; and "A Spot Test for Detection of Lead in Paint" by J. Sayre and D. Wilson, *J. Pediatrics*, vol. 46, pp. 783–785 (1970).

As some of the prior art publications indicate, there is a recognized need in the industry for a simple test or method for determining the presence of lead. However, as will become apparent from the remaining descriptions of the prior art, prior to the present invention, an effective and simple test for lead had not been developed.

In a well known prior art method of detecting lead in paint, sodium sulfide ($Na_2S$) is reacted with lead to form lead sulfide (PbS), a black precipitate. The presence of lead is thus confirmed by the appearance of the black precipitate, lead sulfide. This method has several disadvantages: (1) the sodium sulfide is potentially toxic, especially to young children; (2) the black precipitate is difficult to see on dark surfaces; (3) the sodium sulfide releases volatile hydrogen sulfide ($H_2S$), which has a noxious odor; and (4) the reagents react with many cations to form black precipitates and thus tend to give false readings on many surfaces.

Another common analytical reagent is a metal complexing agent, rhodizonic acid. For over forty years, rhodizonic acid and salts thereof have been used as analytical reagents to detect heavy metals, including lead, in both qualitative and quantitative analyses. The methodology for using rhodizonate dye is based on two types of tests:

(1) a quantitative determination of heavy metals in solutions using a spectrophotometer to obtain quantitative information; and (2) qualitative determinations which use filter papers impregnated with the reagent.

In addition, semi-quantitative information can be derived from the use of columns packed with silica gel impregnated with rhodizonate dye. See U.K. Patent Application No. 2 025 047 A.

The Macherey-Nagel Company (Düren, Germany) manufactures a test paper for the determination of lead under the trademark PLUMBTESMO. The PLUMBTESMO strips comprise a heavy filter paper with a reagent impregnated therein. To test for lead in a solution, a strip is dipped into the solution, and observed for a color change that indicates the presence of lead. The PLUMBTESMO strips can also be used to detect lead deposits in motor vehicle tailpipes. However, the PLUMBTESMO strips are not intended to detect lead in a liquid sample.

The instruction sheet that is distributed with the PLUMBTESMO strips indicates that the PLUMBTESMO strips may be used to detect the presence of lead on a degreased surface. However, the instruction sheet impliedly recognizes that the PLUMBTESMO strips are not entirely satisfactory for testing for the presence of lead on a surface. Specifically, the instruction sheet indicates that the PLUMBTESMO strip may have to be held firmly against a test surface for as long as fifteen minutes before an indication of lead develops. Clearly, for nonprofessional, household use, a test strip that must be held firmly for fifteen minutes is entirely unsatisfactory in that many users will become impatient after only a few minutes and will discontinue the application of the PLUMBTESMO strip against the test surface. That type of usage may, of course, result in dangerous false readings, leaving the user with the erroneous impression that lead is not present when in fact lead may be present.

A further disadvantage of the PLUMBTESMO strips is that the test operator must directly handle the test strips, thus being unnecessarily exposed to chemicals. Yet another disadvantage of the PLUMBTESMO strips is that the strips are flat and comparatively stiff, and are thus not readily conformable to curved or otherwise unusually contoured surfaces, such as those that one is likely to encounter on moldings in older houses.

Thus, it should be clear that the lead tests, known prior to the present invention, are not entirely satisfactory. Therefore, there is a need in the art for a test or method for determining the presence of toxic metals, such as lead and cadmium. Furthermore, there is a need in the art for a test for determining the presence of toxic metals in a liquid sample.

SUMMARY OF THE INVENTION

Accordingly, a major object of the present invention is to provide a method for testing liquid samples for the presence of nutrients or contaminants.

Another object of the present invention is to provide a method for the detection of heavy metal contaminants in a sample, wherein a sample is added to a test bottle, the bottle is capped with a cap containing crushable units of reagents which are able to react with the heavy metal, causing reagents from the crushable units to combine with the sample and a detectable color change occurs which identifies a particular heavy metal contaminant.

Another object of the invention is to provide an apparatus for detecting heavy metal contaminants in a sample, comprising a bottle, a cap, and a crushable reagent container which, upon breaking, releases reagents which react with the heavy metal contaminant to produce a specific colored reaction product.

A further object of the present invention is to provide an all-in-one apparatus for detecting heavy metal contaminants in a sample, including a cap with a porous membrane which separates the crushable reagent container from the sample until the cap is tightened.

A still further object of the present invention is to provide an apparatus for detecting heavy metal contaminants in a sample, wherein the top of the cap is transparent.

A still further object of the present invention is to provide an apparatus for detecting heavy metal contaminants in a sample wherein the crushable reagent capsules are contained in an eye dropper bulb within the cap.

Another object of the present invention is to provide an apparatus for detecting heavy metal contaminants in a sample wherein both an eyedropper and a cap contain crushable reagent capsules.

According to the present invention, a system for detecting a substance in a sample, includes a container for holding the sample to be tested; a cap for closing the container; a chamber within said cap; a reagent within said chamber that forms a visible reaction when exposed to said substance; and means for exposing said reagent to the sample when said container is closed by the cap.

Another system includes a container for holding the sample to be tested; a cap for closing the container; a chamber within said cap; a capsule containing a reagent that forms a visible reaction when exposed to said substance, said capsule being located in said chamber; and means in said cap for opening said capsule and exposing said reagent to the sample when said container is closed by the cap.

A method of detecting a substance in a liquid sample, according to the present invention, includes the steps of providing a reagent that will react with the substance in such a manner so as to give a visual indication of the reaction; providing a solution that will not dissolve in the sample and in which the reagent will dissolve; mixing the reagent, the solution, and the sample together so that the reagent will dissolve in the solution and so that the reagent will be exposed to the sample; observing the reagent that is dissolved in the solution for the visual indication.

Another method of detecting lead in a liquid sample, according to the present invention, includes placing a reagent that will react with lead so as to provide a visual indication of the reaction in a first capsule; placing a solution that will not dissolve in the sample and which will dissolve the reagent in a second capsule; placing the first and second capsules in a container with the sample; opening the capsules in the container so that the reagent will dissolve in the solution and will be exposed to the sample in order to react with any lead in the sample; and observing the reagent for the visual indication.

Another method of detecting a substance in a liquid sample, includes the steps of exposing the sample to a first reagent to cause certain elements therein to precipitate; filtering out the precipitated elements; providing a second reagent that will react with the substance in such a manner so as to give a visual indication of the reaction; providing a solution that will not dissolve in the sample and in which the second reagent will dissolve; mixing the second reagent, the solution, and the filtered sample together so that the second reagent will dissolve in the solution and so that the second reagent will be exposed to the filtered sample; observing the second reagent that is dissolved in the solution for the visual indication.

Yet another method of detecting a substance in a liquid sample, includes the steps of providing a first reagent that causes the substance to precipitate; immobilizing the first reagent on a filter; passing the sample through the filter; providing a second reagent that forms a visible reaction when exposed to the substance; contacting the filter with the second reagent to test for the substance on the filter.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

The test apparatus of the present invention may be used to detect a variety of substances, depending on the reagent contained in the crushable reagent containers. The test apparatus may be used to determine the presence of lead, cadmium, bismuth, mercury, cobalt, arsenic, tin, antimony, iron, aluminum, selenium, copper or organophosphates, among others. Table I identifies a number of potential substances that may be detected using the teachings herein. Appropriate reagents are also set forth in Table I. In addition, the teachings of U.S. Pat. No. 5,039,618, and U.S. Pat. No. 5,330,917 are incorporated herein by reference.

The metals most likely to be detected with the present invention will be lead, bismuth, mercury, arsenic, and copper, among others. The present invention preferably can be used to determine the presence of metals in samples such as drinking water.

The apparatus can be made in a variety of formats as shown in the figures and described below.

Figure 1:
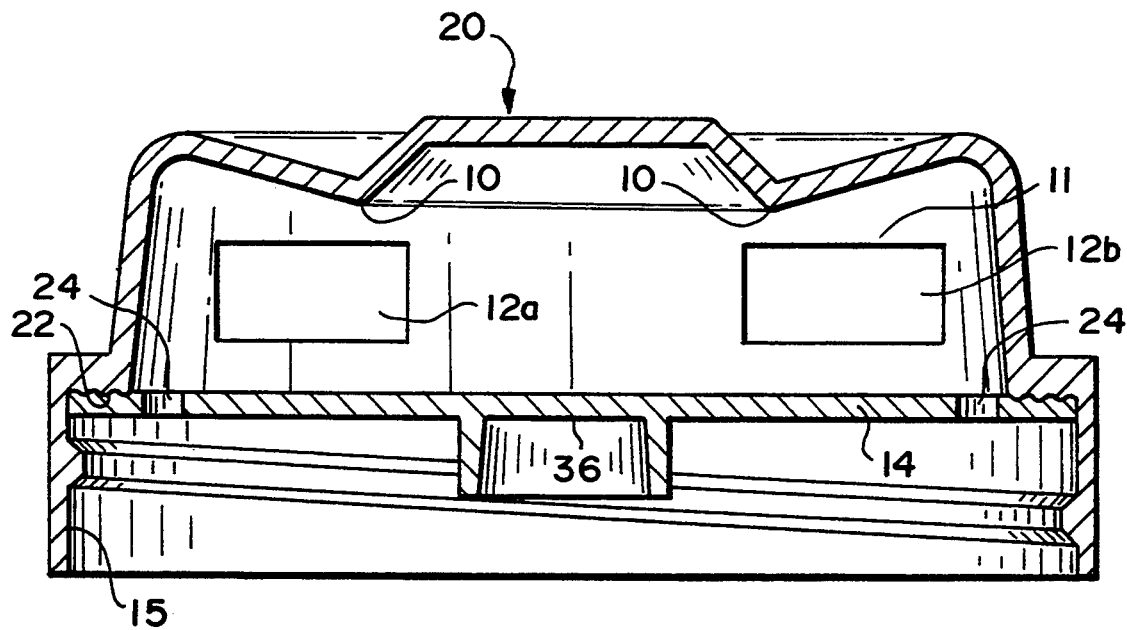
FIG. 1 is cross-sectional view of a cap for a container in accordance with the present invention.

Referring now in detail to the drawings, wherein like reference numerals refer to like elements throughout, in the embodiment of FIG. 1, a cap of the test apparatus is indicated generally by reference numeral 20. The cap 20 is preferably formed from plastic or any other suitable material. If plastic is used, the composition of the plastic is not critical.

The cap 20 includes a capsule chamber 11, in which one or more capsules 12 (or 12a, 12b) of reagents can be stored. The walls of the capsule chamber 11 are preferably made from polypropylene, or some other elastic or deformable material so that the capsules 12 within the chamber 11 can be crushed to release the reagents contained in the capsules 12.

The wall of the capsule chamber 11 may include one or more portions 10 that are shaped so as to facilitate contacting and crushing the capsules 12 within the cap 20.

At the base of the cap 20 is a threaded portion 15 that is designed to engage with a like threaded portion of a jar or container that contains the sample to be tested. Instead of a threaded portion, any acceptable means of sealing the cap 20 to the jar or container may be used.

Figure 2:
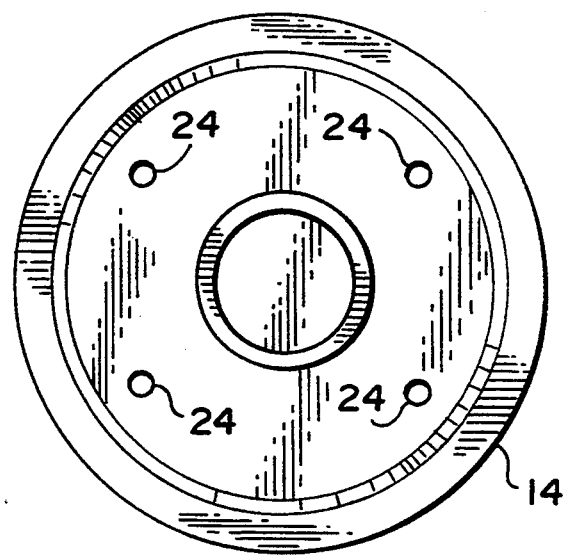
FIG. 2 is a plan view of a plate used in the cap of FIG. 1.

Separating the capsule chamber 11 from the threaded portion 15 is a plate 14, which may also be seen in FIG. 2. The plate 14 fits against a shoulder 22 in the cap 20 so that the plate 14 is secured between the shoulder 22 and a top edge of the jar or container to which the cap 20 is secured, when the cap 20 is secured to the jar or container. The plate 14 includes a plurality of openings 24 to enable the sample in the jar and the reagents in the cap 20 to pass freely therethrough.

The plate 14 may also include a region 36 for painting a dye or some other reagent.

The cap 20 of the present invention may contain one or more separate capsules 12. In one preferred embodiment, two capsules are used. The first capsule 12a contains ammonium citrate, potassium cyanide, hydroxylamine, ammonium hydroxide and dithizone in amounts known to those of ordinary skill in the art. The reaction which occurs includes a color change (blue-green to red) associated with the reaction of lead (if any is present in the sample) and the dithizone dye under the proper conditions of pH, ionic strength and in the presence of cyanide and ammonium ions as chelators. An activator solution typically will be used with the reagent dyes in carrying out embodiments of the present invention. When testing for lead, the pH level is preferably greater than 8.5.

The second capsule 12b contains chloroform, or some other liquid that is capable of dissolving the reagents in the first capsule 12a. Table II identifies solutions that may be used in the second capsule 12b instead of chloroform.

TABLE II

| Dissolvent | pH | COLOR OF BUBBLE |
| --- | --- | --- |
| 1-Bromo-5 Chloropentane 98% | 8 | Teal |
| 2,2-Bromopropane 96% | 6 | cloudy light Amber color |
| 1-Bromo-6-chlorohexane 97% | 8 | Teal |
| 1,3-Dibromobutane 98% | 8 | Amber green |
| 1,3-Dibromobutane 97% | 8 | brownish |
| 1,3-Dibromopropane 99% | 8 | dark amber |
| 1-Bromo-3-chloropropane 99% | 8 | Teal |
| 1,6-Dibromohexane 97% | 8 | Teal |
| 2,3-Dibromobutane 99% | 8 | Teal |

Alternatively, in a second embodiment, three capsules are used. The first capsule is similar to the first capsule 12a described above, except that it does not contain the dithizone. The dithizone is located in a separate capsule. For example, the first capsule may contain ammonium citrate, potassium cyanide, hydroxylamine and ammonium hydroxide, with a second capsule containing the dithizone dye. The third capsule contains chloroform, or some other dissolvent such as those listed in table II. These two or three crushable capsules are located in the capsule chamber 11 of the cap 20.

As will be apparent to those skilled in the art, the specific reagents discussed above are by way of example, not limitation. Other embodiments may be fashioned to test for lead or other substances using different reagents, including, but not limited to those set forth in Table I.

Figure 3:
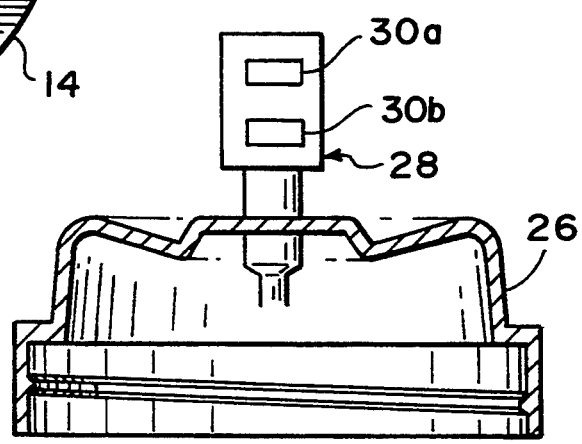
FIG. 3 is an alternative embodiment of a cap for a container in accordance with the present invention.

Turning attention now to FIG. 3, instead of a capsule chamber, a cap 26 may be alternatively equipped with an eye dropper 28 which contains one or more crushable capsules 30a, 30b. The eye dropper can be used together with, or in place of, capsules placed directly in the cap 26. The capsules 30a, 30b in the eyedropper may contain reagents for detecting a specific substance.

For example, the first capsule 30a may contain ammonium citrate, potassium cyanide, hydroxylamine, ammonium hydroxide and dithizone. The second capsule 30b may contain chloroform, or some other liquid that is capable of dissolving the reagents in the first capsule 30a. See Table II for a list of possible dissolvants that may be used instead of chloroform. In addition, as set forth above with respect to an earlier example, the dithizone may be omitted from the first capsule 30a and included by itself in a third capsule.

Figure 4:
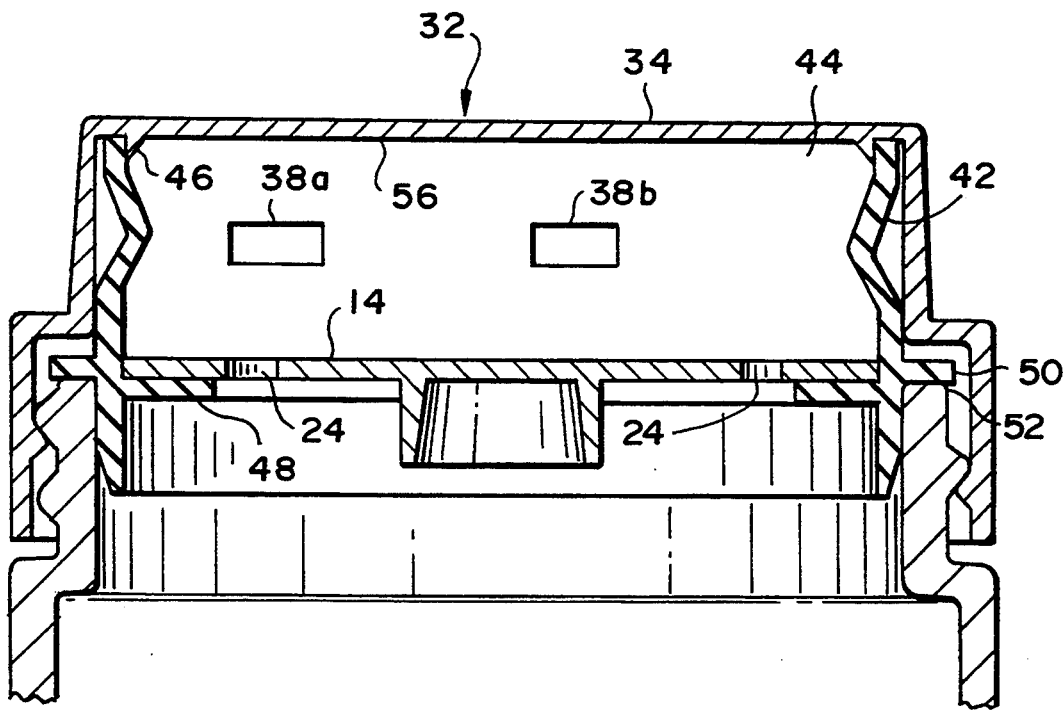
FIGS. 4, 5, and 6 are alternative embodiments of a cap for a container in accordance with the present invention.

The cap assembly may be designed in several alternative ways. One such embodiment is illustrated in FIG. 4. A cap 32 includes a substantially rigid section 34 that forms a chamber 44 in which capsules 38a, 38b are located. To test for lead, the first capsule 38a may contain ammonium citrate, potassium cyanide, hydroxylamine, ammonium hydroxide and dithizone. The second capsule 38b may contain chloroform, or some other liquid that is capable of dissolving the reagents in the first capsule 38a. Table II identifies solutions that may be used in the second capsule 38b. In addition, as set forth above with respect to an earlier example, the dithizone may be omitted from the first capsule 38a and included by itself in a third capsule.

To test for substances other than lead, reagents, including, but not limited to, those listed in Table I may be used in the capsules.

The cap 32 further includes a threaded portion 40 for threadably engaging with a similarly threaded portion on a jar or container 54 to which the cap is to be attached.

An elastomeric sleeve 42 is mounted to the interior of the cap 32 so as to define the chamber 44 for retaining the capsules 38a, 38b. An annular ridge 46 may be provided on the interior surface of the cap to facilitate securing the elastomeric sleeve 42 to the cap 32.

A plate 14 is mounted on an annular shelf 48 that may be integrally formed extending inwardly from the elastomeric sleeve 42. The plate 14 further defines, along with the sleeve 42 and the interior top surface 56 of the cap 32, the capsule chamber 44. As illustrated in FIG. 2, the plate 14 includes a plurality of apertures 24 allowing the sample in the container 54 to mix with the reagents in the capsule chamber 44.

The sleeve 42 further includes a second annular shelf 50 that extends outwardly from the sleeve 42. The second shelf 50 engages with a top surface 52 of the container 54 to which the cap is attached. When the cap 32 is threaded tightly onto the container 54, the top surface 52 of the container 54 urges the second shelf 50 toward the capsule chamber 44. As a result, there is a collapsing action of the elastomeric sleeve 42 (illustrated in FIG. 4), which draws the plate 14 toward the interior top surface 56 of the cap 32. As the plate 14 is drawn toward the top surface 56, the capsules 38a, 38b in the capsule chamber 44 are crushed, thus releasing the reagents therein.

The capsules 38a, 38b illustrated in FIG. 4 are shown disproportionately small. In actual practice, the capsules would be large enough so that they would likely be crushed when the plate 14 and top surface 56 are in the relative positions illustrated in FIG. 4.

In the foregoing embodiments, after the capsules are crushed, the chloroform does not mix with the sample of water. Instead, the chloroform forms a "bubble" in the sample. In addition, the other reagents from the capsules are dissolved in the chloroform and are thus retained within the bubble. The bubble of chloroform thus retains the reagents in a concentrated location of the sample for easier reading, as opposed to allowing the reagents to be uniformly dispersed throughout the sample.

If more than a certain concentration of lead is present in the sample, the color of the reagents will change from blue-green to red, as the lead reacts with the dithizone. The concentration of the lead level in the sample can be determined from the color intensity by comparing the color against known standards or reading the color with a spectrophotometer. With the present invention, 10 parts per billion (of lead to water) can be detected reliably. In some cases, concentrations as low as 3 to 5 parts per billion can be detected. Below is a table of various quantities of sample, dissolvant, and reagent that can be used in accordance with the present invention. The quantities set forth in Table III are exemplary and are not intended to limit the scope of the present invention.

TABLE III

| Amount of sample (ml) | Amount of dissolvant (ml) | Amount of reagent (mg) |
| --- | --- | --- |
| 10 | 0.25 | 0.125 |
| 60 | 1 to 3 | 0.6-1.5 |
| 125 | 1 to 3 | 0.6-1.5 |
| 250 | 1 to 3 | 0.6-1.5 |
| 500 | 1 to 3 | 0.6-1.5 |
| 1000 | 1 to 3 | 0.6-1.5 |

The concentration of lead in the sample necessary to create a detectable reaction with the reagents depends upon not only the concentration of reagent in the dissolvant (e.g., chloroform), but also upon the ratio of sample to dissolvant. The ratio of sample to dissolvant is preferably about 20:1, but could be much higher.

Figure 5:
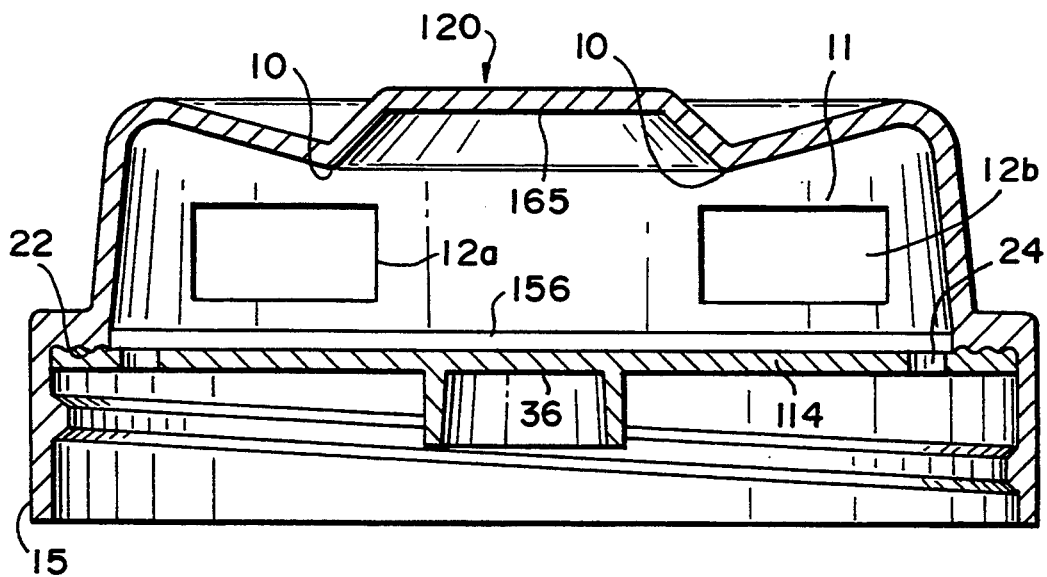

For various reasons, primarily related to improving visibility of the bubble, one or more phase separating membranes may be used. For example, FIG. 5 illustrates a cap 120 that is substantially similar to the cap 20 illustrated in FIG. 1, except as described below. In the cap 120, a phase separating membrane 156 is provided between the plate 114 and the top surface 165 of the cap 120. The phase separating membrane 156 is designed to allow the water sample to pass therethrough, but does not allow the chloroform to pass through it. The membrane 156 allows the liquid sample from the container to pass into the capsule chamber 111 so that the sample can be exposed to the reagents. However, the phase separating membrane 156 prevents the bubble that includes the reagents dissolved therein from passing through into the container. By retaining the bubble of reagents within the capsule chamber 111, the bubble can be kept in a location where it can be more easily seen by a user.

Two or more phase separating membranes can be used to trap the bubble in a specific location for enhanced visibility.

Figure 6:
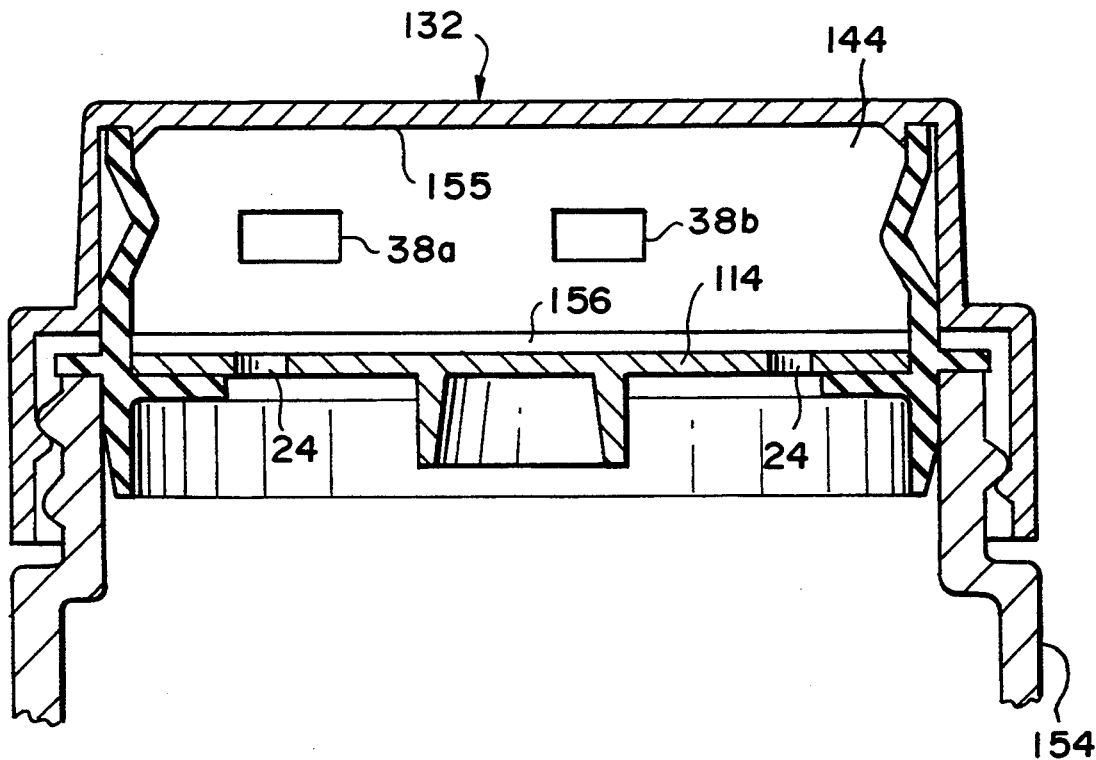

FIG. 6 illustrates a cap 132 that is substantially similar to the cap 32 illustrated in FIG. 4, except as described below. In the cap 132, a phase separating membrane 156 is provided between the plate 114 and the top surface 155 of the cap 132. The membrane 156 allows the liquid sample from the container 154 to pass into the capsule chamber 144 so that the sample can be exposed to the reagents. However, the phase separating membrane 156 prevents the bubble that includes the reagents dissolved therein from passing through into the container. By retaining the bubble of reagents within the capsule chamber 144, the bubble can be kept in a location where it can be more easily seen by a user.

Two or more phase separating membranes can be used to trap the bubble in a specific location for enhanced visibility.

Although FIGS. 5 and 6 illustrate the use of a phase separating membrane in specific embodiments of the present invention, one or more phase separating membranes can be used in any of the embodiments disclosed herein in order to trap the bubble in a location where it can be easily read.

In addition, the cap may include a clear portion, placed in conjunction with one or more phase separating membranes in order to enhance visibility of the bubble. For example, the top surface of the cap may be clear.

In the embodiments of the present invention set forth above, the first capsule includes potassium cyanide in order to prevent a visible reaction between the dithizone and substances such as bismuth, cadmium, and zinc. If the potassium cyanide is omitted, for example for safety reasons, the reagents will indicate a reaction with lead, bismuth, cadmium, and zinc. Since zinc is the only reactable substance in that list that is not toxic, an alternative embodiment has been developed to prevent a reaction with zinc.

In that embodiment, the sample is first mixed with quinaldic acid. If necessary the mixture is heated or boiled. Any other reagents capable of precipitating zinc may be used instead of quinaldic acid. Any zinc present in the sample is precipitated and can then be removed from the sample by any known means, such as pouring the mixture through a filter. The remaining sample is then tested for lead by any known means, including the method described above, i.e., using ammonium citrate, hydroxylamine, ammonium hydroxide, and dithizone in one capsule and using chloroform or some other dissolvant in a second capsule. It is also possible that the dithizone can be omitted from the first capsule and be included by itself in a third capsule. The capsules can be included in a cap of any of the types disclosed herein.

In that case, a visible reaction will occur if the sample includes any of lead, bismuth, or cadmium.

Figure 7:
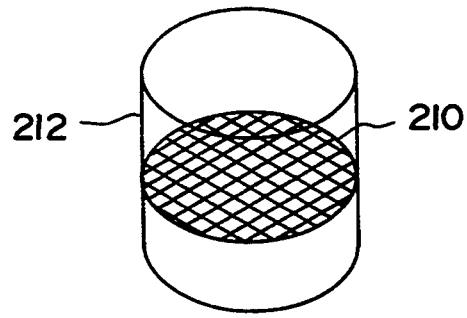
FIG. 7 is a perspective view of an aerator used in the present invention.

In another alternative embodiment of the present invention, a filter 210 is removably fixed within some sort of fluid passageway, such as an aerator 212. See FIG. 7. The filter is treated with immobilized quinaldic acid to precipitate out any zinc present in the sample. The treated sample is then tested for lead in any known manner, including by the method described above, i.e., using ammonium citrate, hydroxylamine, ammonium hydroxide, and dithizone in one capsule and using chloroform or some other dissolvant from Table II in a second capsule. It is also possible that the dithizone can be omitted from the first capsule and be included by itself in a third capsule. The capsules can be included in a cap of any of the types disclosed herein.

In that case, a visible reaction will occur if the sample includes any of lead, bismuth, or cadmium.

In another embodiment, the filter 210 is treated with immobilized chromate or iodide in order to precipitate out and trap any lead present in the sample. Any other capable of precipitating lead may be used instead of the chromate or iodide. After passing the sample through the filter, the filter is then tested by some known means to determine if it contains lead. For example, a lead test swab treated with rhodizonate dye, such as those disclosed in U.S. Pat. No. 5,039,618, may be used to detect the presence of lead on the filter.

Although only preferred embodiments are specifically illustrated and described herein, it will be appreciated that many modifications and variations of the present invention are possible in light of the above teachings and within the purview of the appended claims without departing from the spirit and intended scope of the invention. Specifically, the present invention is not limited to tests for the presence of lead.

TABLE I

| Metal | Dye (Reagent chich Reacts with Metal | Activating Solution | Color |
|---|---|---|---|
| Bi | Cinchonine - KI (1%) | Dilute acid | Orange Red |
| Hg | 1) Diphenylcarbazide (1% in alcohol) | 0.2 M $HNO_3$ | Violet |
| | 2) Cobalt (II) thiocyanate test | Cobalt (II) acetate | Deep blue |
| Sb | 1) Rhodamine B (Tetraethylrhodamine) | $Sb^{+5}$ nitrite | Blue |
| | 2) 2,2'-bipyridine or 1,1' bis(4-phenly-sulfonic acid) | thioglycolic acid buffer | Red |
| Al | 1) Aurin tricarboxylic acid | NaOH | Red |
| | 2) Quinolizarin | Ammonia, then glacial HONC | Red |
| Se | Pyrrole reagent | 0.5 M iron (III) chloride; $H_3PO_4$ | Green-Blue |
| organo-phosphates | Phosphomolybdic acid formed with sodium molydbate | 1) $K_2SO_8 + K_2SO_4$ 2) Ascorbic Acid | Blue |
| Cu | 1) Quinolyl reagent (0.2 g/l in amyl alcohol) | 20 g Na acetate 10 g K Na tartrate 3 g hydroxy-ammonium Cl (all in 100 ml $H_2O$) | Red |
| | 2) Dithiooxamide (1% in acetone) (Rudeanic acid) | | Dark-Green |
| Co | Rudeanic acid chloride | Ammonia/alkali tartrates | Brown |
| Sn | Sodium sulfide | dilute acid | Brown ($Sn^{+2}$)/ Yellow ($Sn^{+4}$) |
| Cd | 4-nitronaphthalene-diazoamine-azo-benzene | sodium potassium tartrate, sodium acetate, sodium citrate at pH 8.5 | pink |

What is claimed is:

1. A system for detecting a substance in a sample, comprising:
    a container for holding the sample to be tested;
    a cap for closing the container;
    a chamber within said cap;
    a crushable first capsule containing a reagent that forms a visible reaction when exposed to said substance, said first capsule being located in said chamber;
    a phase separating membrane in said cap to retain the reagent within the cap; and
    means for exposing said reagent to the sample when said container is closed by the cap.

2. The system of claim 1, further comprising means within said cap to facilitate crushing the capsule.

3. The system of claim 1, wherein the substance is one of lead, bismuth, cadmium, and zinc.

4. The system of claim 1, wherein the substance is one of lead, bismuth, and cadmium.

5. The system of claim 1, wherein the substance is lead.

6. The system of claim 1, wherein the reagent includes dithizone.

7. The system of claim 6, wherein the first capsule also includes ammonium citrate, hydroxylamine, and ammonium hydroxide.

8. The system of claim 1, further including a second crushable capsule in the chamber, wherein said second capsule includes a solution for dissolving the reagent.

9. The system of claim 8, wherein the solution is not dissolvable in the sample.

10. A system for detecting a substance in a sample, comprising:
    a container for holding the sample to be tested;
    a cap for closing the container;
    a chamber within said cap;
    a capsule containing a reagent that forms a visible reaction when exposed to said substance, said capsule being located in said chamber;
    a phase separating membrane in said cap to retain the reagent within the cap; and
    means in said cap for opening said capsule and exposing said reagent to the sample when said container is closed by the cap.

11. The system of claim 10, wherein the substance is one of lead, bismuth, cadmium, and zinc.

12. The system of claim 10, wherein the substance is one of lead, bismuth, and cadmium.

13. The system of claim 10, wherein the substance is lead.

14. The system of claim 13, further including a second capsule that includes a solution for dissolving the reagent.

15. The system of claim 10, wherein the capsule is crushable.

16. The system of claim 15, further including a second crushable capsule in the chamber, wherein said second crushable capsule includes a solution for dissolving the reagent.

17. The system of claim 10, wherein the reagent includes dithizone.

18. The system of claim 17, wherein the first capsule also includes ammonium citrate, hydroxylamine, and ammonium hydroxide.

19. The system of claim 18, wherein the first capsule also includes potassium cyanide.

20. The system of claim 10, wherein the opening means includes a plate that is drawn toward a top surface of the chamber when said cap is placed on the container.

21. The system of claim 20, wherein the opening means includes a flexible seal between the plate and a wall of said chamber to prevent the reagent from leaking from the container.

22. The system of claim 20, further including a second capsule that includes a solution for dissolving the reagent.

23. A method of detecting a substance in a sample, comprising the steps of:
    placing a sample in a container;
    providing in a cap for the container a crushable capsule containing a reagent that forms a visible reaction when exposed to the substance;
    providing a solution which is not dissolvable in the sample and in which the reagent will dissolve in a second crushable capsule in the cap of the container, and dissolving the reagent in the solution so as to concentrate the reagent in a bubble of the solution within the sample;
    closing the container with the cap; and
    exposing the reagent to the sample by crushing the capsules after the cap is put on the container; and
    observing the bubble for an indication of a reaction between the reagent and the substance.

24. The method of claim 23, wherein the reagent is in a capsule and the exposing step includes crushing the capsule after the container is put on the cap.

25. The method of claim 23, wherein the substance is lead.

26. A system for detecting a substance in a sample, comprising:
    a container for holding the sample to be tested;
    a cap for closing the container;
    a chamber within said cap;
    a crushable first capsule containing a reagent that forms a visible reaction when exposed to said substance, said first capsule being located in said chamber;
    a crushable second capsule located in the chamber containing a solution for dissolving the reagent, wherein the solution is not dissolvable in the sample so as to concentrate the reagent within a bubble of the solution within the sample; and
    means for detecting the substance in the sample by exposing said reagent to the sample when the container is closed by the cap.

* * * * *